(12) United States Patent
Turner

(10) Patent No.: US 8,785,842 B2
(45) Date of Patent: Jul. 22, 2014

(54) ION MOBILITY SPECTROMETER INCLUDING SPACED ELECTRODES FOR FILTERING

(71) Applicant: Richard Turner, Cambridge (GB)

(72) Inventor: Robert Brian Turner, Cambridge (GB)

(73) Assignee: Smiths Detection-Watford Ltd., Watford, Hertfordshire (GB)

( * ) Notice: Subject to any disclaimer, the term of this patent is extended or adjusted under 35 U.S.C. 154(b) by 0 days.

(21) Appl. No.: 13/659,629

(22) Filed: Oct. 24, 2012

(65) Prior Publication Data

US 2013/0284911 A1    Oct. 31, 2013

Related U.S. Application Data

(63) Continuation of application No. 12/598,213, filed as application No. PCT/GB2008/001470 on Apr. 25, 2008, now Pat. No. 8,299,423.

(30) Foreign Application Priority Data

May 1, 2007 (GB) .................................. 0708391.8

(51) Int. Cl.
*H01J 49/00* (2006.01)
(52) U.S. Cl.
USPC ........... 250/281; 250/282; 250/290; 250/292; 250/293
(58) Field of Classification Search
USPC .......................... 250/281, 282, 290, 292, 293
See application file for complete search history.

(56) References Cited

U.S. PATENT DOCUMENTS

| 7,119,328 B2 | 10/2006 | Kaufman et al. |
| 7,368,709 B2 | 5/2008 | Guevremont et al. |
| 2004/0056191 A1 * | 3/2004 | Jenkins et al. ................. 250/287 |
| 2005/0029449 A1 * | 2/2005 | Miller et al. ................... 250/293 |

FOREIGN PATENT DOCUMENTS

| WO | 2005059518 | 6/2005 |
| WO | WO 2005059518 A2 * | 6/2005 |
| WO | 2005086742 | 9/2005 |

* cited by examiner

*Primary Examiner* — Michael Maskell
(74) *Attorney, Agent, or Firm* — Reinhart Boerner Van Deuren s.c.

(57) ABSTRACT

An ion mobility spectrometer has an inlet for an analyte substance opening into an ionization region that produces ions of the substance. Parallel grid electrodes extend laterally across the ion flow path and apply an electric field to the ions that is switchable between a relatively low magnitude alternating field that varies in magnitude over multiple periods and an asymmetric alternating field of sufficiently high magnitude to cause differential mobility effects. A collector collects the passed ions, and an indication of the nature of the analyte substance is produced from the collected ions passed during both the low and high field intervals. Also disclosed is the application of a substantially alternating field between the electrodes, which field varies between a low value and a higher value over a time exceeding that of the alternating period.

20 Claims, 3 Drawing Sheets

ION MOBILITY SPECTROMETER INCLUDING SPACED ELECTRODES FOR FILTERING

CROSS-REFERENCE TO RELATED APPLICATION

This patent application is a continuation of U.S. patent application Ser. No. 12/598,213, filed on Oct. 30, 2009, entitled "Ion Mobility Spectrometer Including Spaced Electrodes for Filtering," now U.S. Pat. No. 8,299,423, granted on Oct. 30, 2012, which is assigned to the assignee of the present patent application and which is hereby incorporated herein by reference in its entirety.

BACKGROUND OF THE INVENTION

Field of the Invention

This invention relates to detection apparatus of the kind including spaced electrodes having a source of a substantially symmetric alternating field connected to apply the field between the electrodes.

Conventional ion mobility spectrometers (IMS) are used to provide an indication of the nature of a gas or vapor by determining the mobility of ions of the analyte substance at relatively low electrical fields, where ion mobility follows a linear relationship with changes in field magnitude. An alternative form of ion mobility spectrometer called a FAIMS (field asymmetric ion mobility spectrometer) or differential mobility spectrometer (DMS) makes use of much higher fields to provide an indication of the nature of analyte ions from the manner in which the mobility of certain ions deviates from the linear relationship with changes in field magnitude at high fields. Both IMS and FAIMS spectrometers have advantages and disadvantages, with an IMS being better suited for detecting certain substances and a FAIMS being better suited for detecting certain other substances. The maximum amount of information about ions, and hence the maximum selectivity, would be obtained by measuring ion mobility at both high and low fields. This could be achieved by connecting a high field detector and a low field detector together in tandem, but this creates various engineering problems. Furthermore, such a combined instrument would be relatively bulky and would have relatively high power requirements.

It is accordingly desirable to provide an alternative method and apparatus for detection, and an alternative spectrometer.

The subject matter discussed in this background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

SUMMARY OF THE INVENTION

According to one aspect of the present invention, there is provided detection apparatus of the above-specified kind, characterized however in that the magnitude of the field varies between a low value and a higher value over a time exceeding the time of the alternating period, wherein the maximum magnitude is less than that required to cause differential ion mobility effects, and wherein the apparatus includes a collector for collecting ions passed through the field to produce an output signal that varies as ions of different low-field mobilities are passed through the electrodes or are captured between them, together with a processor that is responsive to the output signal to provide an indication of the ions detected.

The electrodes may be arranged laterally with respect to the ion flow path through the apparatus, and they may be of an open construction such that the ions can pass through them. The collector may be arranged to collect those ions passing through the electrodes. Alternatively, the electrodes may be arranged parallel to the ion flow path through the apparatus such that the ions pass along a gap between the electrodes. In the alternative arrangement, the collector is arranged to collect those ions passed along the length of the gap between the electrodes. The apparatus may also be arranged to apply a high field asymmetric alternating field to the electrodes at time different from the time the symmetric alternating field is applied, the high field being sufficient to cause high field differential mobility effects such that the apparatus can be arranged to provide indications of both the high field mobility and the low field mobility of analyte ions.

According to another aspect of the present invention, a detection apparatus includes spaced electrodes and a voltage source, wherein the voltage source is arranged to apply both low and high alternating fields to the electrodes to produce separate indications of both the low field mobility and the high field mobility of detected ions, wherein the apparatus includes a processor that is arranged and configured to provide an indication of the nature of the detected ions using both of the mobility indications.

According to a further aspect of the present invention, a method of detecting ions is provided that includes supplying analyte ions for detection between two electrodes and applying two different fields between the electrodes at different times, one field being a relatively low symmetric alternating field that increases in magnitude over a time exceeding the period of the alternating field, the other field being a relatively high asymmetric alternating field sufficient to cause high field differential mobility effects in the ions, and then collecting ions passed through the electrodes during the application of both fields and providing an indication of the nature of the ions collected from signals produced by the collected ions during both the low and high fields.

According to a fourth aspect of the present invention there is provided a spectrometer having an inlet for an analyte substance and an ionization region arranged to produce ions of the substance and to supply those ions to an electric field region, wherein the electric field region is switchable between two different fields, namely a relatively low magnitude alternating field that varies in magnitude over multiple periods and an asymmetric alternating field of sufficiently high magnitude to cause differential mobility effects.

The electric field region may be provided between two grid electrodes extending either transversely across the path of flow of the ions or in a gap between two electrodes extending along the path of flow of the ions.

DESCRIPTION OF THE DRAWINGS

Two different forms of spectrometer and methods of detecting substances constructed and operating according to the present invention will now be described, by way of example, with reference to the accompanying drawings, in which.

DETAILED DESCRIPTION OF THE PREFERRED EMBODIMENT

Figure 1:
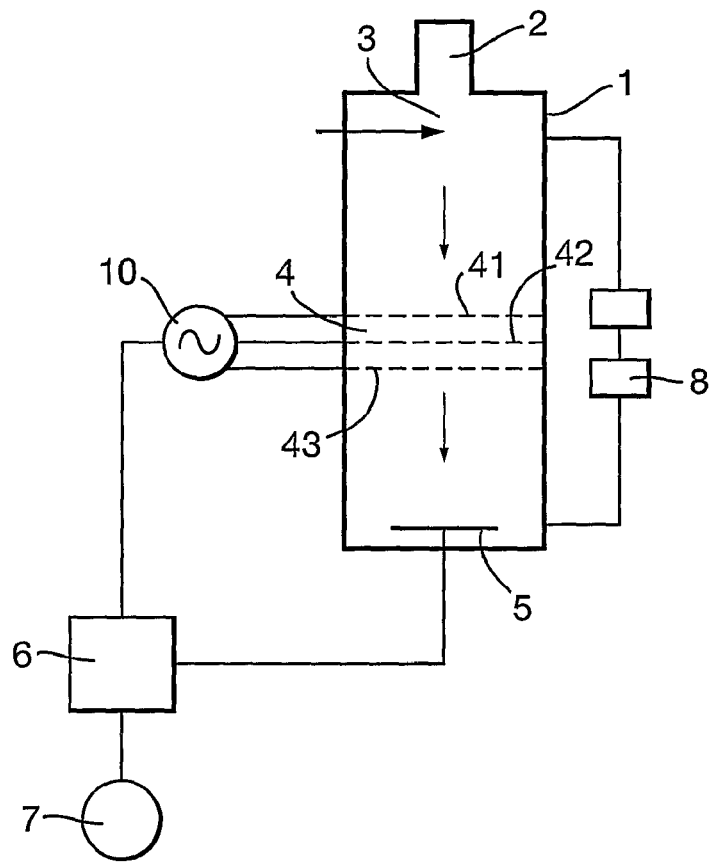
FIG. 1 is a schematic view of a parallel-motion spectrometer.

Referring first to FIG. 1, a detection apparatus is shown in the form of a spectrometer having a housing 1 with an inlet 2 located at its upper end for admitting an analyte substance in the form of a gas or vapor. The inlet 2 opens into an ionization region 3 where the molecules of admitted analyte substance are ionized. The ions that are produced flow down the spectrometer under the influence of an electric field or a gas flow to an electric field region 4. The electric field region 4 is provided by two or three parallel grid-like electrodes 41, 42, and 43 extending laterally across the housing 1, the open nature of the electrodes 41, 42, and 43 being such that neutrally charged ions can pass through the electrodes 41, 42, and 43 substantially unhindered. A collector plate 5 that is located below the field region 4 is connected to an amplifier and processing unit 6, which in turn provides an output to a display or other utilization means 7. A gas flow system, indicated generally by the numeral 8, is connected between opposite ends of the housing 1 of the spectrometer to provide a flow of clean dry gas along the housing 1, as required.

The electrodes 41, 42, and 43 are connected to a voltage source oscillator 10 that is selectively operable to apply two different electrical fields to the electrodes 41, 42, and 43. The first field is of relatively low magnitude. In this description of the present invention, the term "low field" is used to indicate fields where the mobility of ions varies in a linear manner with changes in field magnitude. The field is produced by applying a square wave to the electrodes 41 to 43 that alternates symmetrically between equal positive and negative voltages. The amplitude of the square wave is modulated so that it increases linearly from zero to a maximum value over a time equal to many oscillation periods of the square wave. This causes the ions between the electrodes 41 to 43 to oscillate backwards and forwards between the electrodes 41 to 43. Those ions with a high mobility have a relatively large amplitude of movement, whereas those ions with a lower mobility have a lower amplitude, as shown by the two traces depicted in FIG. 2, with the dotted line representing ions of a high mobility and the solid line representing ions of a low mobility. The separation between the electrodes 41 to is represented by the horizontal dashed line "S" positioned against the vertical, displacement scale, which is in arbitrary units.

Figure 2:
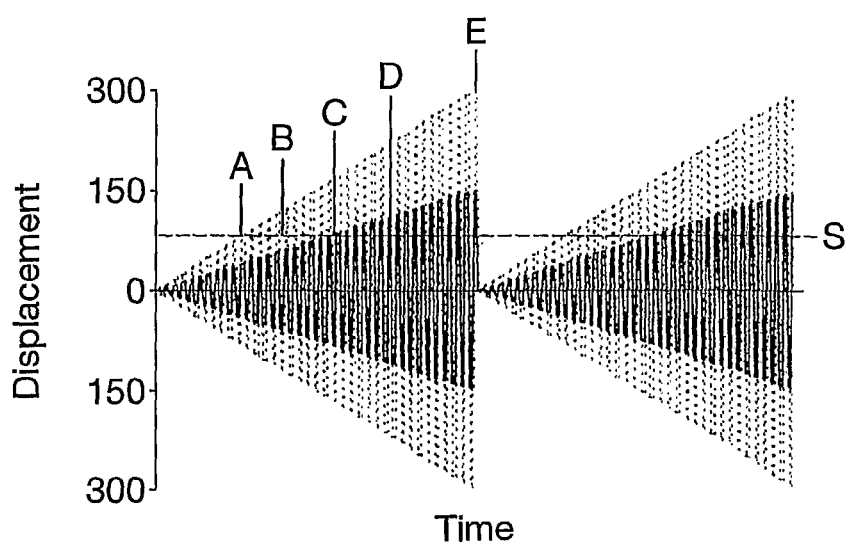
FIG. 2 shows movement of high-mobility and low-mobility ions when subject to a relatively low alternating field of increasing magnitude.
Figure 3:
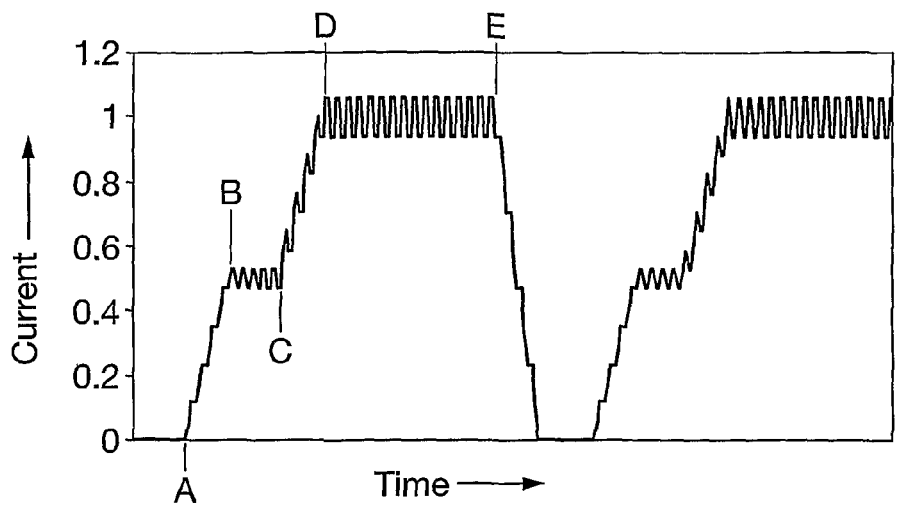
FIG. 3 illustrates the ion current produced by the low magnitude field plotted against time.

The ion current produced is represented in FIG. 3, which has been smoothed to reduce fluctuations from the high frequency rectangular waveform. In fact, most amplifiers configured for low noise will produce this form of smoothing. It can be seen, therefore, that, at low fields, all the ions will oscillate between the confines of the electrodes 41 to 43 and none will pass through, so there will be a zero ion current. As the field increases further (at point "A" in FIGS. 2 and 3), initially, only the higher mobility ions will reach and pass through the lower electrode 43 and, therefore, pass to the collector plate 5 where it is detected. The ion current, therefore, increases steadily as more high mobility ions pass through. Eventually (at point "B" in FIGS. 2 and 3), all the high mobility ions pass through the lower electrode 43, so the current reaches a plateau. Further increase in the amplitude of the oscillating field then starts to drive the lower mobility ions through the lower electrode 43 (at point "C" in FIGS. 2 and 3), so the ion current again rises to a new plateau (at point "D" in FIGS. 2 and 3), where all of the low mobility ions are being driven through the lower electrode 43. When the field falls to zero again (at point "E" in FIGS. 2 and 3), at the end of the cycle, the ion current also drops to zero. It will be appreciated that, in general, there will be a range of ions with ion mobility between the two extremes. The maximum field value is selected according to the separation between the electrodes 41 to 43. It is set such that the slowest mobility ions likely to be met will be passed through the lower electrode 43 at some point below the maximum field value. The processor 6 is arranged to identify the characteristics of the curve shown in FIG. 3, which provides information about the nature of the detected ions. The curve shown in FIG. 3 may be used in this form, or it may be differentiated, as shown in FIG. 4, to make the identification of the characteristics even clearer.

Figure 4:
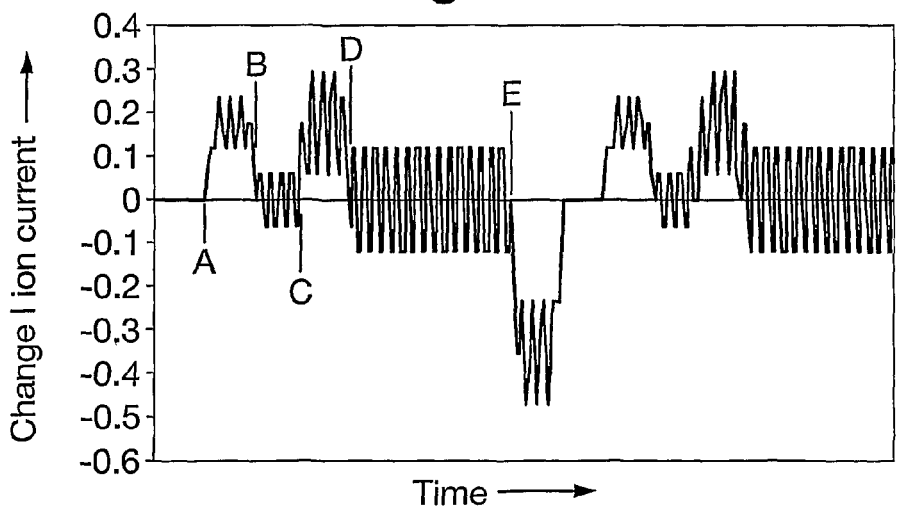
FIG. 4 shows the differentiated ion current output of FIG. 3.

Variations in the signal caused by the oscillating field can be seen in FIGS. 2 and 4. To minimize this, it is desirable to have the highest possible ratio between the modulation frequency and the frequency of the oscillating field. The frequency of the modulation sweep might typically be in the range 1 Hz to 10 Hz, giving 1 spectra to 10 spectra per second. The oscillating waveform, which need not be rectangular, would typically have a frequency in the region of kHz.

Figure 5:
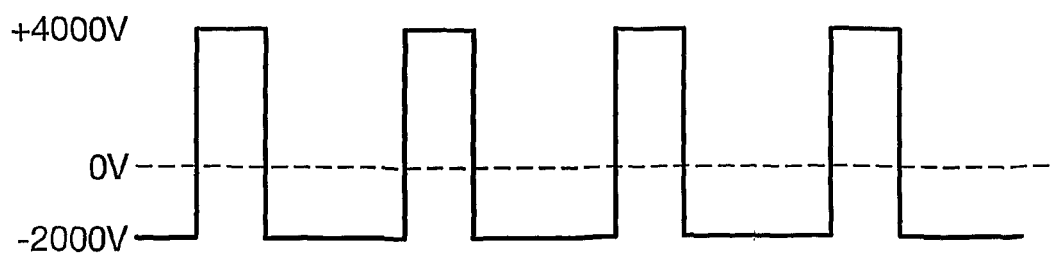
FIG. 5 shows a high magnitude asymmetric field used in the spectrometer instead of the low magnitude field.

Information from the low field mode may, in some cases, be used by itself to identify the nature of the detected ions, such as by correlation with a look-up table of the curve characteristics of known ions. Alternatively, and according to an aspect of the present invention, this information may be combined with information about the high field mobility derived using the same apparatus operated in a high field mode, as described below. To derive the high field information, the oscillator 10 is switched to a high field mode to provide a voltage of the kind shown in FIG. 5. Instead of using the same oscillator, the high field could be provided by a different oscillator (not shown in the figures). In this application, the term "high field" is used to indicate a field that is high enough to cause differential mobility effects in ions. The voltage shown in FIG. 5 is a conventional FAIMS asymmetric voltage comprising short duration high voltage positive pulses and longer duration lower voltage negative pulses. The duration and magnitude of the positive and negative pulses are selected such that the mean voltage over one cycle is zero. In this example, the voltage switches between +4000 volts and −2000 volts, the duration of the negative part of the cycle thus being twice the duration of the positive part of the cycle. This gives a field between the electrodes 41 to 43 on the order of tens of thousands of volts/cm. When operated in this mode, ions without high field differential mobility have a net zero displacement, so they will remain between the electrodes 41 to 43. Those ions that do have different mobility at high fields will, however, gradually move towards one or other of the electrodes, according to their charge, and eventually pass through the electrode. The system is arranged such that the ions to be detected move through the lower electrode 43, and hence pass to the collector plate 5 for detection. Small DC voltages can also be superimposed on electrodes 41, 42, and 43, and ions with various differential mobilities can be selected and identified by adjusting these voltages. Alternatively, the DC voltages on the electrodes can be fixed and the differential mobility of ions can be measured by measuring the time they take to pass through from electrode 41 to electrode 43. Techniques that combine these two approaches can also be used.

Thus, by operating the spectrometer in both the low field mode and the high field mode, it is possible to extract two different indications of the nature of the ions, or, alternately, it is possible to identify both ions with a characteristic low field mobility and those with a characteristic high field mobility. The processor 6 uses the information from the two modes to provide an improved indication of the nature of the analyte substance.

Similar measurements can also be made using spectrometers employing just two grids, such as grids 41 and 42 or 42 and 43 in FIG. 1.

Figure 6:
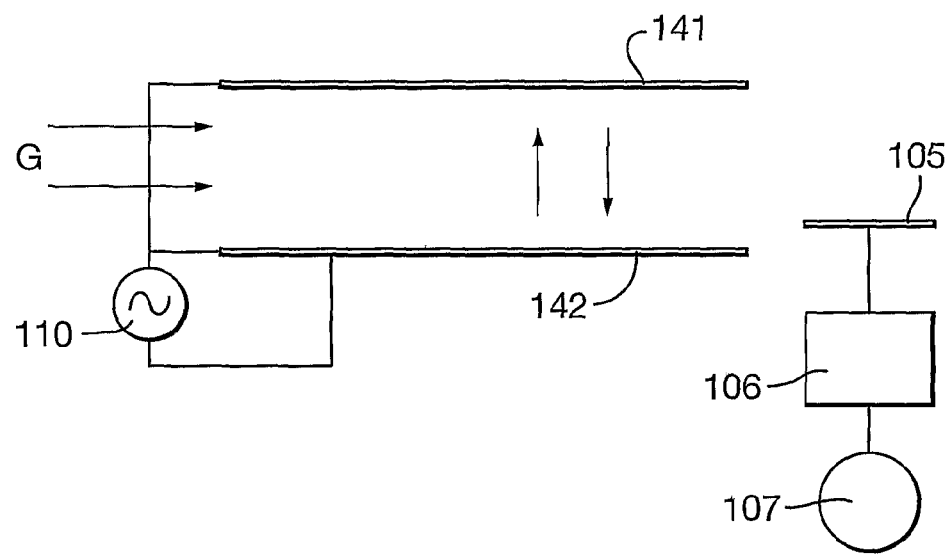
FIG. 6 is a schematic view of a portion of an alternative form of spectrometer.
Figure 7:
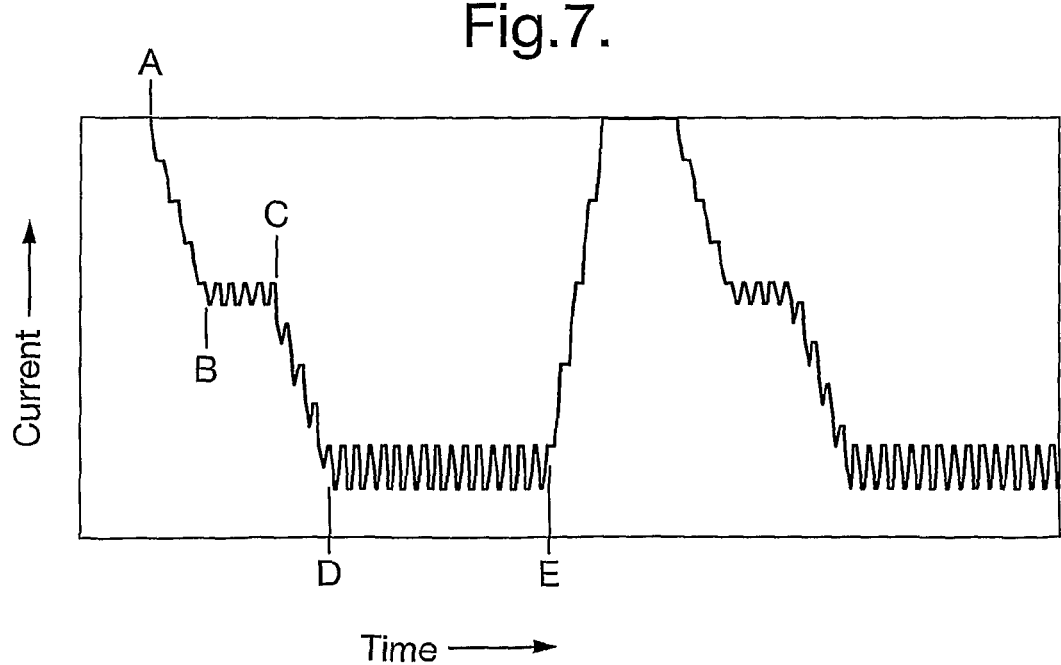
FIG. 7 illustrates the ion current produced by the spectrometer of FIG. 6 when operated in the low field mode plotted against time.

It is not essential for the spectrometer to be arranged to produce parallel ion motion by the use of open, grid electrodes arranged transverse to the ion flow direction in the manner shown in FIG. 1. Instead, it could be arranged in a manner similar to a conventional FAIMS instrument, as shown in FIG. 6, where components equivalent to those in FIG. 1 have been given the same reference numeral with the addition of 100. In this arrangement, the electrodes 141 and 142 are arranged parallel to the axis of the instrument and to the direction of gas flow "G" through the instrument. The electrodes 141 and 142 may be provided by two parallel, solid, flat plates, as shown, or they could instead be provided by two coaxial tubular electrodes, as is well known in FAIMS instruments. The same low voltage field is applied between the two electrodes 141 and 142 as in the arrangement of FIG. 1, and this field produces the same oscillating motion of the low and high mobility ions shown in FIG. 2. At the low fields, the amplitude of oscillation between the electrodes 141 and 142 is relatively small so the ions do not contact the electrodes, thereby allowing them to flow along the gap between the electrodes and out of the right-hand end of the electrodes (as shown in FIG. 6) to the collector plate 105 for detection. The change in ion current with time is represented in FIG. 7. As the amplitude of oscillation increases with increasing applied field, the higher mobility ions start to impact the electrodes 141 and 142 and be lost, causing a drop in the ion current (at point "A" in FIG. 7) detected at the collector plate 105. Ion current falls as the field strength increases until all of the higher mobility ions impact the electrodes 141 and 142 and there is a plateau (at point "B" in FIG. 7). Subsequently (at point "C" in FIG. 7), the lower mobility ions start to impact the electrodes 141 and 142 and the ion current again starts to fall until (at point "D" in FIG. 7) all of the lower mobility ions impact the electrodes 141 and 142 and there is a plateau in the ion current until the start of the next cycle at point "E" in FIG. 7.

When operated in the high field FAIMS mode, a voltage of the kind shown in FIG. 5 is applied to the electrodes 141 and 142 in place of the low field voltage. Ions with a differential high field mobility drift towards one or other of the electrodes 141 or 142 and do not, therefore, pass along the gap between the electrodes for detection by the collector plate 105. By applying a DC voltage to the alternating voltage, selected ions can be passed through the electrodes 141 and 142 for detection in the manner of a conventional FAIMS instrument. Again, by combining the outputs derived when the instrument is operating in its low field mode and in its high field mode, it is possible to obtain increased information about the ions from the same instrument, thereby giving enhanced selectivity.

The low field arrangement of the present invention avoids the need for the pulsed operation, which is usual in conventional time-of-flight instrument, and which is relatively inefficient because not all of the ions are analyzed.

The apparatus may be arranged to switch between the high field mode and the low field mode at regular intervals. Alternatively, it may operate in one mode and be manually switched to the other mode as desired. The apparatus could operate in one mode and automatically switch to the other mode only when the first mode gives an ambiguous output or suggests the presence of a substance that is better suited to detection in the alternative mode.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be claimed alone or in combination with any of the features, elements, or components of any of the other embodiments discussed above.

What is claimed is:

1. A spectrometer, comprising:
   an ionized analyte flow path from a first end of the spectrometer toward an opposite second end of the spectrometer;
   at least two spaced-apart electrodes located intermediate the first and second ends of the spectrometer;
   a voltage source oscillator that is arranged and configured to be selectively, alternately operable to apply a first electrical field to the electrodes to cause the mobility of ions to vary in a linear manner with changes in the magnitude of the first electrical field, and a second different electrical field to the electrodes to cause high field differential mobility effects in ions; and
   a detector apparatus including a collector located proximate the second end of the spectrometer that collects ions passed through the electrical fields;
   wherein the detector apparatus provides an indication of the ions collected by the collector.

2. A spectrometer as defined in claim 1, additionally comprising:
   a source of clean, dry gas to the first end of the spectrometer that establishes the flow path from the first end of the spectrometer toward the second end of the spectrometer.

3. A spectrometer as defined in claim 1, wherein an analyte is admitted to the spectrometer through an inlet located at the first end of the spectrometer and ionized in an ionization region located adjacent the first end of the spectrometer.

4. A spectrometer as defined in claim 1, wherein the electrodes are arranged and configured to produce ion motion that is parallel to the direction of the flow path when first or send electric fields are applied to the electrodes.

5. A spectrometer as defined in claim 4, wherein the electrodes are arranged and configured laterally of the ion flow path through the detection apparatus and are of an open construction such that ions can pass through them.

6. A spectrometer as defined in claim 5, wherein the collector is arranged and configured to collect those ions passing through the electrodes.

7. A spectrometer as defined in claim 1, wherein the electrodes are arranged and configured to produce ion motion that is lateral to the direction of the flow path when first or send electric fields are applied to the electrodes.

8. A spectrometer as defined in claim 7, wherein the electrodes are arranged and configured parallel to the flow path of ions through the detection apparatus such that ions pass along a gap between the electrodes.

9. A spectrometer as defined in claim 8, wherein the collector is arranged and configured to collect those ions passed along the length of the gap between the electrodes.

10. A spectrometer as defined in claim 1, wherein the first electrical field is a low voltage wherein the mobility of ions varies in a linear manner with changes in the magnitude of the first electrical field, and wherein the second electrical field is a high voltage which is sufficiently high to cause differential mobility effects in ions.

11. A spectrometer as defined in claim 1, wherein the first electrical field is a low voltage wherein the mobility of ions varies in a linear manner with changes in the magnitude of the first electrical field; and
   wherein the first electrical field has a magnitude that varies between a low value and a higher value over a time exceeding that of the alternating period.

12. A spectrometer as defined in claim 1, wherein the first electrical field comprises a relatively low symmetric alternating electrical field that increases in magnitude over a time exceeding the period of the alternating electrical field.

13. A spectrometer as defined in claim 1, wherein the second electrical field is sufficient to cause high field differential mobility effects such that the detection apparatus can be arranged to provide indications of both the high field mobility and the low field mobility of analyte ions.

14. A spectrometer as defined in claim 1, wherein the second electrical field comprises a relatively high asymmetric field sufficient to cause high field differential mobility effects in the ions.

15. A spectrometer as defined in claim 1, wherein the collector produces an output signal that varies as ions of different mobilities are passed through the electrodes or are captured between them.

16. A spectrometer as defined in claim 15, additionally comprising:
   a processor responsive to the output signal to provide the indication of the ions detected by the collector.

17. A spectrometer, comprising:
   a source of clean, dry gas supplied to a first end of the spectrometer that establishes an ionized analyte flow path from the first end of the spectrometer toward an opposite second end of the spectrometer;
wherein an analyte is admitted to the spectrometer through an inlet located at the first end of the spectrometer and ionized in an ionization region located adjacent the first end of the spectrometer;
   at least two spaced-apart electrodes located intermediate the first and second ends of the spectrometer;
   a voltage source oscillator that is arranged and configured to be selectively, alternately operable to apply a first low voltage electrical field wherein the mobility of ions varies in a linear manner with changes in the magnitude of the first electrical field and a second electrical field having a magnitude that varies between a low value and a higher value over a time exceeding that of the alternating period to the electrodes to cause high field differential mobility effects in ions;
   a collector located proximate the second end of the spectrometer that collects ions passed through the electrical fields and produces an output signal that varies as ions of different mobilities are passed through the electrodes or are captured between them; and
   a processor responsive to the output signal to provide an indication of the ions detected by the collector.

18. A spectrometer, comprising:
an ionized analyte flow path in the spectrometer;
two spaced-apart electrodes located intermediate the first and second ends of the spectrometer;
a voltage source oscillator configures to selectively, alternately apply a first electrical field to the electrodes to cause the mobility of ions to vary in a linear manner with changes in the magnitude of the first electrical field and a second electrical field to the electrodes to cause high field differential mobility effects in ions;
a collector that collects ions passing through the electrical fields; and
a detector apparatus that provides an indication of the ions collected by the collector.

19. A method of detecting ions, comprising:
establishing an ionized analyte flow path from a first end of a spectrometer toward an opposite second end of the spectrometer;
selectively, alternately applying a first electrical field to spaced-apart electrodes located intermediate the first and second ends of the spectrometer with a voltage source oscillator to cause the mobility of ions to vary in a linear manner with changes in the magnitude of the first electrical field, and a second electric field to the electrodes to cause high field differential mobility effects in ions;
collecting ions passed through the electrical fields with a collector located proximate the second end of the spectrometer that; and
providing an indication of the ions collected by the collector with a detector apparatus.

20. A method as defined in claim 19, wherein the first electrical field is a low voltage wherein the mobility of ions varies in a linear manner with changes in the magnitude of the first electrical field; and
   wherein the first electrical field has a magnitude that varies between a low value and a higher value over a time exceeding that of the alternating period.

* * * * *